US00PP12837P2

(12) United States Plant Patent
van Noort

(10) Patent No.: US PP12,837 P2
(45) Date of Patent: Aug. 6, 2002

(54) LEUCANTHEMUM PLANT NAMED 'SUNNY SIDE UP'

(75) Inventor: Marcus Wilhelmus Gerardus van Noort, Warmond (NL)

(73) Assignee: Witteman & Co. 'Multiflora' B.V., Hillegom (NL)

( * ) Notice: Subject to any disclaimer, the term of this patent is extended or adjusted under 35 U.S.C. 154(b) by 0 days.

(21) Appl. No.: 09/840,802

(22) Filed: Apr. 25, 2001

(51) Int. Cl.[7] ..... A01H 5/00
(52) U.S. Cl. ..... Plt./285
(58) Field of Search ..... Plt./285

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Leucanthemum plant named 'Sunny Side Up', characterized by its upright plant habit; daisy-type inflorescences; and white-colored ray florets and yellow-colored disc florets.

2 Drawing Sheets

BACKGROUND OF THE INVENTION

The present Invention relates to a new and distinct cultivar of Leucanthemum plant, botanically known as *Leucanthemum maximum* and hereinafter referred to by the name 'Sunny Side Up'.

The new Leucanthemum is a naturally-occurring whole plant mutation of an unidentified selection of *Leucanthemum maximum,* not patented. The new Leucanthemum was discovered by the Inventor in a controlled environment in Warmond, The Netherlands, within a population of plants of the unidentified selection of *Leucanthemum maximum* in 1998. The selection of this new Leucanthemum was based on its inflorescence form and large disc. Compared to plants of the parent selection, plants of the new Leucanthemum have many more ray and disc florets per inflorescence.

Asexual reproduction of the new Leucanthemum by vegetative tip cuttings was first conducted in Warmond, The Netherlands in 1997. Asexual reproducton by cuttings has shown that the unique features of this new Leucanthemum are stable and reproduced true to type in successive generations.

SUMMARY OF THE INVENTION

The cultivar Sunny Side Up has not been observed under all possible environmental conditions. The phenotype may vary somewhat with variations in environment such as temperature, daylength, and/or light level, without, however, any variance in genotype.

The followng traits have been repeatedly observed and are determined to be the unique characteristics of 'Sunny Side Up'. These characteristics in combination distinguish 'Sunny Side Up' as a new and distinct Leucanthemum:

1. Upright plant habit.
2. Large daisy-type inflorescences that are about 7.5 cm in diameter.
3. White-colored ray florets and yellow-colored disc florets.

BRIEF DESCRIPTION OF THE PHOTOGRAPHS

The accompnaying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Leucanthemum.

The photograph at the top of the first sheet comprises a side perspective view of a typical flowering plant of 'Sunny Side Up'. The photograph at the top of the second sheet comprises a close-up view of a typical inflorescence of 'Sunny Side Up'.

The photograph at the bottom of the second sheet comprises a close-up view of the upper surface of a mature leaf of 'Sunny Side Up'.

DETAILED BOTANICAL DESCRIPTION

The following observations, measurements and values describe plants of the new cultivar grown in the field under outdoor conditions during the spring and summer in Warmond, The Netherlands. Plants used in the photographs and the detailed botanical description were about 25 to 35 weeks from planting rooted cuttings. Color references are made to The Royal Horticultural Society Colour Chart, 1995 edition, except where general terms of ordinary dictionary significance are used.

Botanical classification: *Leucanthemum maximum* cultivar Sunny Side Up.

Parentage: Naturally-occurring whole plant mutation of an unidentified seedling selection of *Leucanthemum maximum,* not patented.

Propagation:

*Type.*—Terminal tip cuttings.

*Type cutting.*—Vegetative cuttings.

*Time to produce a rooted liner.*—About 40 days during the spring in Warmond, The Netherlands.

*Root description.*—Fine, fibrous.

Plant description:

*Appearance.*—Upright and broad plant habit. Freely basal branching with about 8 to 10 lateral branches per plant. Moderately vigorous.

*Plant height.*—About 50 cm.

*Plant width.*—About 50 cm.

*Lateral branches*.—Length: About 50 cm. Diameter: About 4 to 7 mm. Internode length: About 1.5 to 5 cm. Strength: Strong. Texture: Immature branches, pubescent; mature branches, glabrous; longitudinally ridged. Color: 143A to 143B.

*Foliage description*.—Arrangement: alternate, simple, sessile. Quantity of leaves per lateral stem: About 13. Length, basal leaves: About 19 cm. Width, basal leaves: About 3 cm. Shape: Narrowly elliptic to elongated oblanceolate. Apex: Acute. Base: Cuneate. Margin: Serrate. Texture, both surfaces: Leathery, rugose, pubescent. Venation pattern: Anastomosing. Color: Young foliage, upper surface: 141A to 143A. Young foliage, lower surface: 143A. Mature foliage, upper surface: 137A. Mature foliage, lower surface: 137C to 138A. Venation, both surfaces: 143C.

Inflorescence description:

*Appearance*.—Daisy-type inflorescence form with elliptic-shaped ray florets. Inflorescences borne on terminals above foliage. Disc and ray florets arranged acropetally on a capitulum. Inflorescences persistent. Not fragrant. Typically one terminal inflorescence per lateral branch.

*Flowering response*.—Under natural conditions, plants flower in the late summer in Warmond, The Netherlands.

*Inflorescence longevity*.—Inflorescences maintain good color and substance for about 3 weeks on the plant.

*Inflorescence bud*.—Height: About 9 mm. Diameter: About 2 cm. Shape: Flattened sphere. Color: 153C.

*Inflorescence size*.—Diameter: About 7.5 cm. Depth (height): About 1 cm. Diameter of disc: About 2.5 cm.

*Ray florets*..—Shape: Elliptic. Orientation: Initially upright, then about 90° from vertical or perpendicular to peduncle. Aspect: Initially incurved, then mostly flat to reflexed. Length: About 2.6 cm. Width: About 9 mm. Apex: Obtuse, emarginate or praemorse. Base: Acute; short corolla tube. Margin: Entire. Texture: Smooth, glabrous. Number of ray florets per inflorescence: About 36 arranged in two rows. Color: When opening, upper and lower surfaces: 157D. Fully opened, upper and lower surfaces: Close to 155D.

*Disc florets*.—Arrangement: Massed at center of receptacle. Shape: Tubular, elongated. Apex: Acute. Length: About 3 mm. Width: About 0.9 mm. Number of disc florets per inflorescence: More than 200. Color: Immature: 13B. Mature: Apex: Close to 7A. Mid-section and base: 155D.

*Phyllaries*.—Quantity/arrangement: About 47 in two to three whorls. Phyllary length: About 8 mm. Phyllary whorl diameter: About 2.9 cm. Shape: Lanceolate to subulate. Apex: Praemorse to obtuse. Margin: Entire. Texture: Smooth, slightly ribbed. Color: Upper surface: 141B. Lower surface: 143A to 143B.

*Reproductive organs*.—Androecium: Present on disc florets only. Stamen quantity: Five. Anther shape: Oval. Anther length: Less than 0.3 mm. Anther color: Close to 7A. Pollen amount: Scarce. Pollen color: Close to 7A. Gynoecium: Present on both ray and disc florets. Pistil quantity: One. Pistil length: About 5 mm. Stigma shape: Bi-lobed. Stigma color: Close to 7A. Style length: About 4.5 mm. Style color: 145C. Ovary color: 145D.

*Seed*.—Length: About 2 mm. Diameter: Less than 1 mm. Color: 200A to 202A.

Disease/pest resistance: Resistance to pathogens and pests common to Leucanthemums has not been observed on plants of the new Leucanthemum.

It is claimed:

1. A new and distinct cultivar of Leucanthemum plant named 'Sunny Side Up', as illustrated and described.

* * * * *

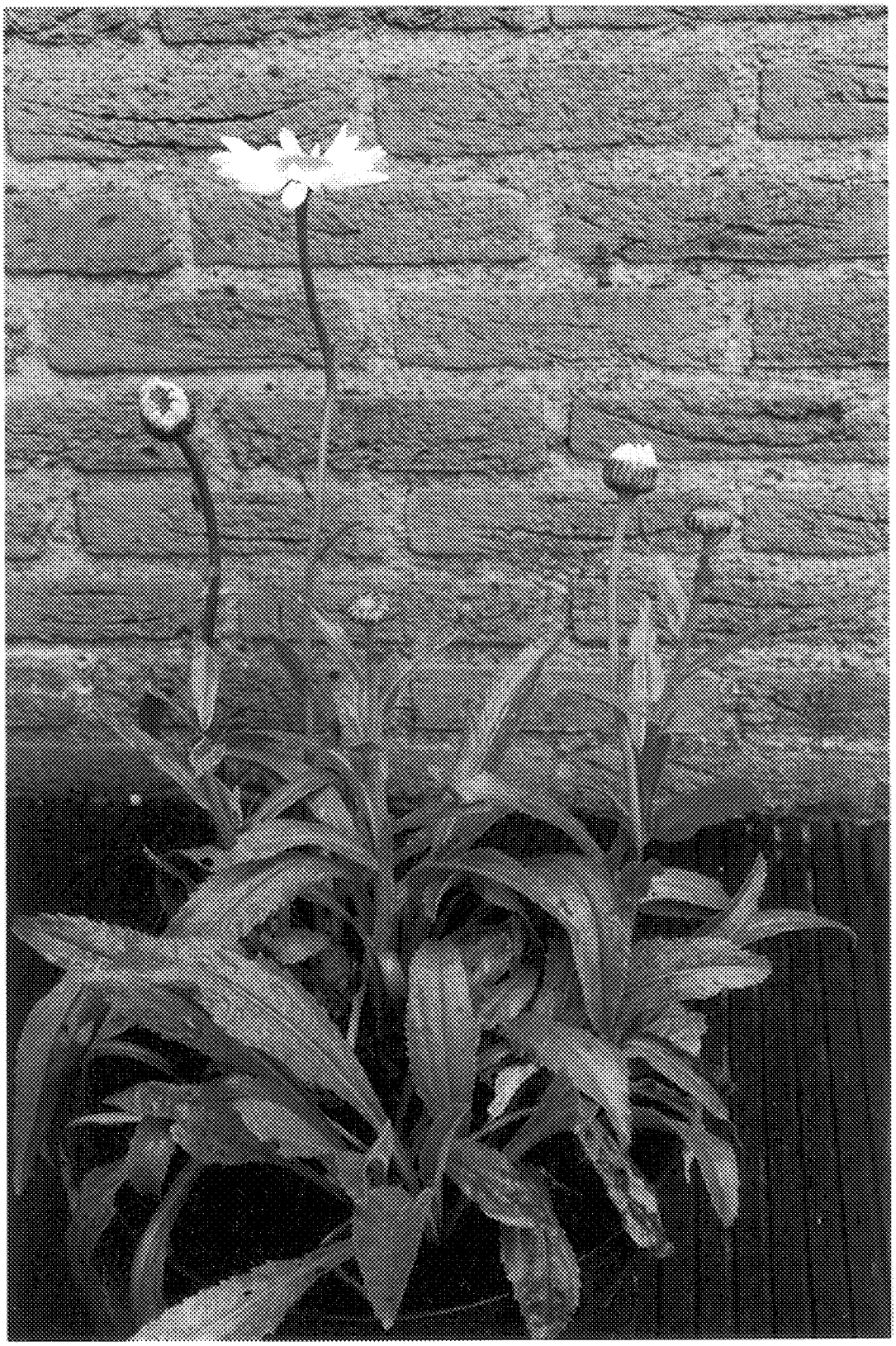

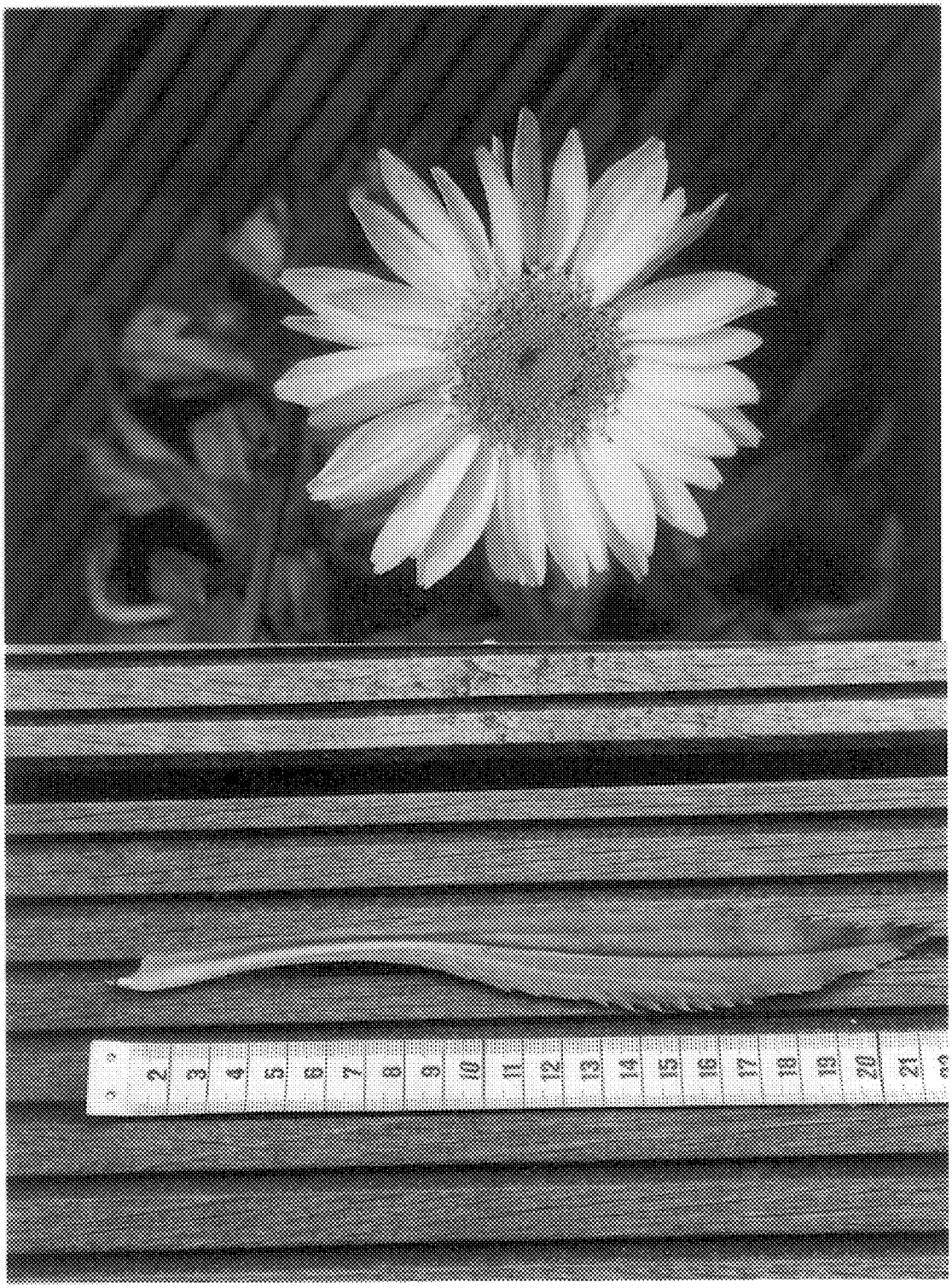
2
3
4
5
6
7
8
9
10
11
12
13
14
15
16
17
18
19
20
21